(12) United States Patent
Knepp

(10) Patent No.: US 7,074,763 B2
(45) Date of Patent: *Jul. 11, 2006

(54) STABLE FORMULATIONS OF NERVE GROWTH FACTOR

(75) Inventor: Victoria M. Knepp, Sunnyvale, CA (US)

(73) Assignee: Syntex (U.S.A.) Inc., Palo Alto, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 09/789,855

(22) Filed: Feb. 20, 2001

(65) Prior Publication Data

US 2001/0007662 A1 Jul. 12, 2001

Related U.S. Application Data

(63) Continuation of application No. 08/418,736, filed on Apr. 7, 1995, now abandoned, which is a continuation-in-part of application No. 08/109,798, filed on Aug. 20, 1993, now Pat. No. 6,277,828.

(51) Int. Cl.
*A61K 38/18* (2006.01)
*C07K 14/48* (2006.01)

(52) U.S. Cl. .......................... 514/12; 530/399

(58) Field of Classification Search ............. 424/583; 514/2, 12, 21; 530/399, 839
See application file for complete search history.

(56) References Cited

U.S. PATENT DOCUMENTS

| 5,096,885 A | 3/1992 | Pearlman et al. ............. 514/12 |
| 5,210,185 A | 5/1993 | DelaValle et al. ........... 530/399 |

FOREIGN PATENT DOCUMENTS

| EP | 0 267 015 | 5/1988 |
| EP | 0 308 238 | 3/1989 |

OTHER PUBLICATIONS

Arakawa et al., "Stabilization of Protein Structure by Sugars", Biochemistry, 21: 6536-6544 (1982).
Calbiochem Catalog, p. 219 (1992).
Diemetal (eds.), "Scientific Tables", Ciba-Geigy, Ltd., Basle, Switzerland, pp. 271-273, 280-281, and 528-529 (1970).
Gregouadis et al., Trends in Biotech., 11: 440-442 (1993).
Pikal, M.J., "Freeze-Drying of Proteins-Part II: Formulation Selection", BioPharm., pp. 26-30, (Oct. 1990).
Pignatti et al., "Solution Properties of β Nerve Growth Factor Protein and Some of its Derivatives", J. Neurochem., 25: 155-159 (1975).
Wang et al., "Parenteral Formulations of Proteins and Peptides: Stability and Stabilizers", J. Parenter. Sci. Tech., 42: S3-S26 (1988).
Allen, S.J., et al, "Recombinant human nerve growth factor for clinical trials: protein expression, purification, stability and characterization of binding to infusion pumps", *J. Biochem Biophys Methods*, 2001, 47:239-55.
Barnett, J., et al., "Physiochemical characterization of Recombinant Human Nerve Growth Factor Produced in Insect Cells with a Baculovirus Vector", *J. Neurochem.*, 1991, 57(3):1052-61.
Bruce, G., et al., "Production and Characterization of Biologically Active Recombinant Human Nerve Growth Factor", *Neurobiol Aging*, 1989 10(1):89-94.
Eng, M. et al, "Formulation Development and Primary Degradation Pathways for Recombinant Human Nerve Growth Factor", *Anal. Chem.*, 1997, 69(20):4184-4190.
Furukawa, Y., et al., "Nerve Growth Factor Secreted by Mouse Heart Cells in Culture", *J. Of Bio. Chem.*, 1984, 259(2):1259-1264.
Harper, G.P., et al, "The Purification of Nerve Growth Factor from Bovine Seminal Plasma", *J. of Bio. Chem.*, 1982, 257(14):8541-8548.
Iwane, M., et al., "Production, Purification and Characterization of Biologically Active Recombinant Human Nerve Growth Factor", *Biochem, Biophys, Res. Commun.*, 1990, 171(1):116-22.
Lam, X.M., et al., "Encapsulation and Stabilization of Nerve Growth Factor into Poly(lactic-co-glycolic) Acid Microspheres", J. Pharm Sci., 2001, 90(9):1356-65.
Pattison, S.E., et al., "On the Relationship of Zinc Ion to the Structure and Function of the 7S Nerve Growth Factor Protein", *Biochemistry*, 1975 (14(12):2733-9.

(Continued)

*Primary Examiner*—Robert C. Hayes
(74) *Attorney, Agent, or Firm*—Grant D. Green

(57) ABSTRACT

Aqueous formulations of nerve growth factor suitable for lyophilization and subsequent reconstitution in which nerve growth factor is admixed with sugars and buffer are provided.

10 Claims, No Drawings

OTHER PUBLICATIONS

Perez-Polo, J.R., et al., "The Preparation and Properties of Nerve Growth Factor Protein at Alkaline pH", *Neurobiology*, 1975, 5(6):329-38.

Yang, T.H., et al., "Effect of Zinc Binding and Precipitation on Structures of Recombinant Human Growth Hormone and Nerve Growth Factor", *J. Pharm. Sci.*, 89(11):1480-5 (2000).

STABLE FORMULATIONS OF NERVE GROWTH FACTOR

CROSS-REFERENCE TO RELATED APPLICATIONS

This application is a continuation of U.S. Ser. No 08/418,736, filed Apr. 7, 1995, now abandoned, which is a continuation in part of U.S. Ser. No. 08/109,798, filed Aug. 20, 1993, now U.S. Pat. No. 6,277,828, the disclosure of which is incorporated by reference herein.

TECHNICAL FIELD OF THE INVENTION

This invention relates to aqueous compositions of nerve growth factor suitable for lyophilization and to the lyophilized products thereof.

BACKGROUND OF THE INVENTION

Numerous polypeptides and proteins regulate the growth or survival of cells; such molecules are termed "growth factors". Examples of growth factors include epidermal growth factor (EGF), acidic and basic fibroblast growth factor (aFGF and bFGF), platelet derived growth factor (PDGF), ciliary neurotrophic factor (CNTF), and nerve growth factor (NGF). Of these, NGF was the first to be identified and characterized (Levi-Montalcini, R., et al., *J. Exp. Zool.*, 116:321, 1951).

NGF promotes the survival and activity of certain types of neuronal cells. In addition, NGF promotes the differentiation of premature neuronal cells into post-mitotic mature neurons.

Purification of NGF from mouse submaxillary gland resulted in-the identification of a complex comprising three subunits, $\alpha$, $\beta$, and $\gamma$. All of the neurotrophic activity of NGF is presumed to reside in the $\beta$ subunit, a 118 amino acid protein having a molecular weight of about 13,000 Da (Varon, S., et al., *Proc. Natl. Acad. Sci. USA*, 57:1782–1789, 1967; Greene, L. A., et al., *Neurobiol.*, 1:37–48, 1971). In solution, $\beta$ subunits form dimers of molecular weight about 26,500 Da.

NGF has been suggested to be effective for treating certain degenerative diseases of both the peripheral and central nervous systems. It has been suggested that the administration of NGF may be beneficial in treating diseases in which a deficiency of NGF, abnormalities of its receptor, or changes in its transport or intracellular processing lead to a decrease in neuronal function, atrophy or even cell death. Such diseases include hereditary sensory and motor neuropathies, hereditary and sporadically occurring system degeneration, amyotrophic lateral sclerosis, Parkinson's disease, and Alzheimer's disease (Goedert, M., et al., *Mol. Brain Res.*, 1:85–92, 1986; Mobley, W. C., et al., *Soc. Neurosci. Abstr.*, 13:186, 1987; Mobley, W. C., et al., *Soc. Neurosci. Abstr.*, 4:302, 1988; Hefti, F., et al., *Ann. Neurol.*, 20:275–281, 1986). NGF is also thought to decrease neuron cell death after exposure to certain toxins, such as 6-hydroxydopamine, (Aloe, L., *Arch. Ital. Biol.*, 113:326–353, 1975), vinblastine and colchicine (Menesini-Chen, M. G., et al., *Proc. Natl. Acad. Sci. USA*, 74:5559–5563, 1977; Johnson, E. M., *Brain Res.*, 141:105–118, 1978) and capsaicin (Otten, U., *Nature*, 301:515–577, 1983).

The high expression of NGF mRNA in the hippocampus, an area associated with memory and leaning, suggests that clinical application of NGF may be effective for the treatment of dementia Kaisho, Y., et al., *Biochem. Biophys. Res. Comm.*, 174:379–385, 1991). The intraventricular administration of NGF has been reported to prevent the death of basal forebrain cholinergic neurons after axotomy suggesting that NGF may be effective in promoting cell survival after injury. (Hefti, F., *J. Neurosci.*, 6:2155–2162, 1986; Williams, L., et al., *Proc. Natl. Acad. Sci. USA*, 83:9231–9235, 1986; Kromer, L., *Science*, 235:214–216, 1987).

The use of NGF for therapy poses significant problems. These problems are associated with 1) maintaining the bioactivity of the NGF, which may be altered during manufacturing, purification, or storage; and 2) administering NGF, a relatively large, hydrophilic molecule, so it reaches the active site in sufficient amounts to be effective. The bioactivity of NGF, like other proteins, is dependent on its secondary and tertiary structure. The $\beta$ subunit of NGF has three internal disulfide bonds, which are thought to be important for bioactivity (Kanaya, E., et al., *Gene*, 83:65–74, 1989; Iwane, M., et al., *Biochem. Biophys. Res. Comm.*, 171:116–122, 1990; Hu, G. -L. and Neet, K. E., *Gene*, 70:57–65, 1988). In addition, to the extent that any of the protein is denatured, the effective amount of biologically active NGP is diminished. Protein integrity must therefore be maintained during manufacture and storage as well as during administration.

Proteins are particularly prone to degradation at elevated temperatures. Lower temperatures generally decrease protein degradation. However, it is more economical to store the protein at room temperature, i.e., about 25° C., rather than at refrigerated temperatures of about 4° C. Therefore, formulation stability is desirable for storage at either room temperature or refrigeration at approximately 4° C.

In addition to problems of stability, NGF, like many other proteins, binds nonspecifically to surfaces. Such nonspecific binding may occur to a variety of materials including glass and plastics, for example polyethylene or polypropylene. These materials may be in the form of vials, tubing, syringes, implantable infusion devices or any other surface which may come in contact with NGF during its manufacture, storage or administration.

Other difficulties in administering proteins such as NGF as therapeutics are poor absorption by the body and degradation by stomach acids. Oral administration is therefore generally unsuitable. Injections and infusion of such proteins may be necessary to overcome such absorption barriers.

Injection is useful when the site of treatment is readily accessible. However, if the site is relatively inaccessible such as the CNS, continuous infusion may be more practical for long term administration. Such administration has been impractical due to various complications. For example, continuous infusion may be achieved by implanting NGF pumps into the brain, but long term exposure of a protein to body temperature often causes degradation of the protein. Also, there may be additional losses due to protein adsorption to the pump chamber over time.

In addition to the problems associated with the administration of NGF, there are also problems associated with its long term storage from the time of manufacture to administration. Lyophilization is one method of long term storage of biological proteins, impeding degradation, aggregation, and/or nonspecific adsorption. However, the lyophilization process itself presents difficulties. As the volume of liquid decreases during the freezing process, the effective salt concentration increases dramatically, which may denature the protein, reducing effective therapeutic activity upon reconstitution. In addition, formation of ice crystals during the freezing process may cause denaturation and also decrease the effective amount of bioactive NGF available. The formulation then must be such as to prevent salt concentration fluctuations and minimize formation of ice crystals.

One object of this invention is to provide formulations of NGF in which bioactivity is maintained after lyophilization and reconstitution. Another object of the invention is to provide methods of storing biologically active NGF.

SUMMARY OF THE INVENTION

The formulations of this invention suitable for lyophilization comprise aqueous solutions of:
(a) nerve growth factor;
(b) a biologically acceptable bulking agent; and
(c) buffer to maintain the pH of the formulation from about 5.5 to about 6.5.

Optionally, a biologically acceptable, water soluble carrier and/or a salt may be present.

Further embodiments of this invention are the lyophilized formulations from which the water has been substantially removed. Upon reconstitution with a reconstituting vehicle, optionally including a biologically acceptable carrier, the formulations of this invention are suitable for use, such as raising antibodies, screening receptors, or administering to patients having conditions responsive to NGF therapy.

DETAILED DESCRIPTION OF THE INVENTION

As used herein, "biologically acceptable" applies to materials characterized by the absence of adverse biological effects in vivo. "Room temperature" is between about 22° C. to about 25° C. "Body temperature" is between about 36° C. to about 40° C. "Lyophilizable formulation" refers to an aqueous formulation of NGF which may be freeze dried to a moisture content preferably less than about 2%, and which retains at least about 70% of the initial NGF bioactivity upon reconstitution. "Isotonic" refers to a solution having approximately the same osmotic pressure as blood serum, about 300 millimols per liter. A "carrier" is any biologically acceptable emulsifier, dispersing agent, surfactant, or protein which decreases adsorption of NGF to a surface.

The term "formulation" refers to a composition of nerve growth factor and any adjuvants, buffers, carriers, stabilizers, and such other additives deemed necessary to maintain acceptable levels of activity and stability of the NGF during storage, handling, and use. The formulations of this invention are useful for the long term storage of NGF.

"NGF" denotes any form of biologically active nerve growth factor, preferably the β subunit of human nerve growth factor. The term NGF also includes hybridized and modified forms of NGF which bind to the NGF receptor and retain NGF bioactivity. Modified forms of NGF may include fusion proteins such as those described in Iwai, S., et al., *Chem. Pharm. Bull.*, 34:4724–4730, 1986 and Kanaya, E., et al., *Gene*, 83:65–74, 1989, and NGF fragments and hybrids in which certain amino acids have been deleted or replaced while maintaining NGF bioactivity and receptor binding.

The preferred form of NGF is human NGF (hNGF). The most preferred form of hNGF is recombinant hNGF (rhNGF). Methods of obtaining NGF suitable for use in the formulations of this invention are known to those skilled in the art. For example, suitable rhNGF may be produced by a baculovirus expression system (Barnett, J., et al., *Exp. Neurol.*, 110:11–24, 1990; EPO 370,171), a yeast expression system (Kanaya, E., et al., *Gene* 83:65–74, 1989), a mammalian cell (CHO) expression system (Iwane, M., et al., *Biochem. Biophys. Res. Comm.*, 171:116–122, 1990), a COS expression system (Bruce, G., et al., *Neurobiol. Aging*, 10:89–94, 1989), or bacterial expression system (Iwai, S., et al., *Chem. Pharm. Bull.*, 34:4724–4730, 1986). The NGF should be at least 65% pure; preferably at least 85% pure; more preferably at least 95% pure; and most preferably at least 98% pure. The purity of isolated NGF for use in the formulations may be determined by silver-stained SDS-PAGE or other means known to those skilled in the art.

In the lyophilizable NGF formulations provided, NGF comprises from about 0.0001 to about 0.125% by weight of the aqueous composition which corresponds to between about 1 to about 1250 µg/ml. More preferably NGF is present in an amount from about 0.001 to about 0.10% by weight (10 to 1000 µg/ml) of the aqueous formulation. Even more preferably NGF is present in an amount from about 0.01 to about 0.10% (100 to 1000 µg/ml) by weight of the aqueous formulation. Most preferably NGF is present in an amount from about 0.01 to about 0.05% (100 to 500 µg/ml) by weight of the aqueous formulation.

The lyophilized formulations of this invention are particularly useful for providing long term storage of NGF, especially at elevated temperatures. The lyophilizable formulations of this invention comprise NGF, a biologically acceptable bulking agent, a buffer to maintain the pH of the formulation from about 5.5 to about 6.5, optionally, a biologically acceptable salt, optionally, a biologically acceptable, water soluble carrier, and water.

The bulking agent generally provides mechanical support by allowing the matrix to maintain its conformation during and after the freeze-drying process. One or more sugars may be used as the bulking agent. Sugars, as used herein, include, but are not limited to, monosaccharides, oligosaccharides and polysaccharides. Examples of suitable sugars include, but are not limited to, fructose, glucose, mannose, sorbose, xylose, maltose, lactose, sucrose, and dextran. Sugar also includes sugar alcohols, such as mannitol, sorbitol, inositol, dulcitol, xylitol and arabitol. Mixtures of sugars may also be used in accordance with this invention.

A preferred bulking agent comprises a combination of sugars. The preferred bulking agent is a combination of sucrose and mannitol. Without being bound by theory, sucrose is thought to form an amorphous glass upon freezing and subsequent lyophilization, allowing for potential stability enhancement of the protein (e.g. prevention of aggregation) by forming a molecular dispersion of NGF in a rigid glass. Stability may also be enhanced by virtue of the sugar acting as a replacement for the water lost upon lyophilization. The sugar molecules rather than the water molecules become bonded to the protein through hydrogen bonds. Mannitol when mixed in a 1:1 mass ratio with sucrose (which has a glass transition temperature of −36° C.) raises the glass transition temperature of the formulation by 5° C. to −31° C. This considerably shortens the primary drying time of the formulation during lyophilization, while still allowing for an amorphous, glassy formulation matrix, and thus is considered an advantage in a large scale manufacturing setting. Other bulking agents which also possess these characteristics may be substituted for one or both of these sugars.

The formulations of this invention which are to be lyophilized preferably have a higher pH than the formulations which are not lyophilized or that are reconstituted. The bulking agents (sugars) which are present in the lyophilizable formulations of the invention are generally more stable at higher pH. Preferably the pH of the formulation prior to lyophilization is between about 5.5 to about 6.5. More preferably the pH of the lyophilizable NGF formulation is between about 5.8 to about 6.2. The pH of the most preferred lyophilizable NGF formulation is about 6.0. When sucrose is present as the bulking agent, the preferred pH of the lyophilizable formulation is about 6.0 since at acidic pH, sucrose, a non-reducing disaccharide, hydrolyzes to the reducing sugars D-fructose and D-glucose. Citrate is the most preferred buffer for lyophilizable NGF formulations but other biologically acceptable buffers may be used, such as maleate. Buffers other than acetate are preferred because of the tendency of acetic acid to volatize during lyophilization. It should be recognized that adjustment of the final pH with acid or base may be necessary. Any loss in long-term stability of aqueous NGF due to the higher pH of about 6.0 is likely to be overcome by the increase in stability associated with the NGF being lyophilized.

Ideally, the choice of buffer takes into account potential pH shifts during lyophilization caused by sequential crystallization of buffer components. For example, with phosphate buffers, the basic component has a higher eutectic point than the acidic component, hence it crystallizes out first and the pH drops. Citrate buffer is preferred because it is thought that both buffer components have about the same eutectic point, resulting in very little pH fluctuation as the temperature drops. Other suitable buffers would have components with the same, or similar eutectic points. The preferred amount of buffer will vary depending on the type of buffer used and its buffering capacity. The buffer should be present in the formulation in an amount sufficient to maintain the final pH of the formulation in the preferred pH range. The preferred concentration of buffer for stable NGF formulations is about 0.01 to about 0.3% by weight of the aqueous formulation (0.1 to 3.0 mg/ml), a more preferred concentration is about 0.1 to about 0.25% buffer by weight of the aqueous formulation (1.0 to 2.5 mg/ml), and the most preferred buffer concentration is about 0.2% buffer by weight of the aqueous formulation (2.0 mg/ml).

The formulation comprises water in an amount sufficient to achieve the appropriate concentration of formulation components.

The lyophilizable formulations also optionally comprise a biologically acceptable salt. The preferred salt is sodium chloride (NaCl) but other biologically acceptable salts may be used, such as potassium chloride (KCl), calcium chloride ($CaCl_2$) and magnesium chloride ($MgCl_2$). The salt may be one salt or a combination of salts. A preferred formulation comprises about 0.5 to 1.0% (i.e., 5 to 10 mg/ml) salt by weight of the aqueous formulation. A more preferred formulation comprises about 0.6 to 0.9% salt by weight of the formulation. More preferably, the formulation comprises about 0.7 to 0.9% salt by weight of the aqueous formulation. The most preferred formulation comprises about 0.87% (i.e., 8.7 mg/ml) salt by weight of the aqueous formulation. Because the salt concentration may increase during lyophilization, it may be desirable to reduce the concentration of salt present in the lyophilizable formulations to prevent protein denaturation. Reductions in salt concentration in the lyophilizable formulation may be compensated for during reconstitution so as to provide a final formulation sufficiently isotonic to be suitable for administration into an individual.

The lyophilizable NGF formulations optionally include carriers. The presence of the carrier in the formulation reduces or prevents NGF adsorption to various surfaces. The need for carrier depends upon the concentration of NGF in the aqueous composition. At sufficiently high (greater than about 500 µg/ml) NGF concentrations, enough NGF remains in solution to offset that which is lost due to surface adsorption. Suitable carriers include, but are not limited to, polysorbates such as Tween® 80, poloxamers such as Pluronic® F68, and proteins such as serum albumin. The preferred carrier is a protein. Human serum albumin (HSA) is particularly preferred. The weight ratio of NGF to carrier is from about 0.0001:1 to about 1:1. A more preferred weight ratio is from about 0.01:1 to about 1:1. The most preferred weight ratio of NGF to carrier is about 0.01:1 to about 0.5:1. Accordingly, when HSA is used as the carrier, the preferred concentration of HSA is from about 0.1 to about 1.25% by weight (i.e., 1 to 12.5 mg/ml) of the aqueous formulation. A preferred formulation is about 0.3 to 0.7% HSA by weight of the aqueous formulation, more preferably about 0.4 to 0.6% HSA by weight of the aqueous formulation. The most preferred formulation is about 0.5% (i.e., 5 mg/ml) HSA by weight of the aqueous formulation.

The preferred lyophilizable formulations comprise about 1 to 1250 µg/ml NGF, 15 to 45 mg/ml sucrose, 15 to 45 mg/ml mannitol, and 0.1 to 0.7 mg/ml citric acid at a pH of about 5.5 to about 6.5. The most preferred lyophilizable formulations of NGF comprise about 100 µg/ml NGF, about 30 mg/ml sucrose, about 30 mg/ml mannitol, about 5 mg/ml human serum albumin, and about 0.3 mg/ml citric acid. The most preferred pH of the lyophilizable formulation is about 6.0.

The lyophilizable formulations of this invention are lyophilized to a residual moisture content of less than about 5%, however, formulations which retain NGF biological activity at higher or lower amounts of moisture content are also contemplated.

The preferred lyophilized formulation comprises 0.001 to 1.25 parts nerve growth factor, 30 to 90 parts sugar, and less than about 1 part water.

The lyophilized NGF formulation is reconstituted with a diluent, containing a buffer, such as citric acid, and salt, such as sodium chloride, as required so the resulting reconstituted formulation comprises about 1 to 1250 µg/ml NGF, 1 to 12.5 mg/ml HSA, 5 to 10 mg/ml NaCl, 0.2 to 3.0 mg/ml citric acid, 1.5 to 30 mg/ml sucrose and 1.5 to 30 mg/ml mannitol, pH 5.2.

The lyophilized NGF formulations of this invention are also useful as components of kits to provide a convenient and economical way of providing stable lyophilized NGF in a form which may be rapidly and easily reconstituted in an appropriate vehicle for administration to a patient in need of treatment. In addition to the lyophilized NGF formulations, the kits of this invention also comprise a reconstituting vehicle. The reconstituting vehicle comprises sterile water and a sufficient amount of salt to make the final reconstituted formulation essentially isotonic. The reconstituting vehicle may further comprise additional buffer. The total volume of reconstituting vehicle present in the kit should be sufficient to achieve a final NGF concentration suitable for administration to an individual in need of treatment. In a preferred embodiment of this invention a kit comprising two vials is provided. One vial comprises the sterile lyophilized NGF formulation of this invention and a second vial comprises sterile reconstituting vehicle. To use the kit, an appropriate amount of reconstituting vehicle is transferred to the vial comprising the lyophilized NGF formulation. Upon dissolution of the lyophilized formulation, the reconstituted formulation may be immediately administered to the patient.

Because of the long term stability of the reconstituted formulation of this invention it is also possible to prepare enough reconstituted formulation to provide multiple doses.

Assay Procedures

Identification and Quantitation of NGF Using Reverse Phase HPLC

NGF was identified and quantified by analyzing 100 µl samples with a reverse phase HPLC (Hewlett Packard HP 1090 Liquid Chromatograph) equipped with a 4–6 mm×25 cm L Dynamax 300 Å 5 µm Analytical Reversed-Phased column (Rainir Instrument Co. Woburn, Mass.) with a Dynamax 300 Å 5 µm 4.6 mm×1.5 cm guard column and a diode array UV detector set at 220 nm. The mobile phases were (A) 0.1% trifluoroacetic acid in water and (B) 0.1% trifluoroacetic acid in acetonitrile where the gradients changed from 25% (B) to 60% (B) in 45 minutes with a flow rate of 0.5 ml/min at a pressure of 1700–2000 psi at ambient temperature.

Identification of NGF was established by comparing its retention time in the sample with the respective retention time of freshly prepared calibrated standard NGF solutions made from NGF from the same lot. The quantity of NGF in the samples was calculated by comparison to a standard curve obtained with serial dilutions of known concentrations.

Determination of NGF Concentration (µg/ml) by ELISA

NGF concentrations were also assayed by ELISA. Both standards and samples were assayed in triplicate. Each plate contained a complete standard curve of NGF and reference blanks without NGF.

After 100 µl of coating antibodies (mouse monoclonal 24Cl raised against rhNGF) was added to each of the wells of a 96 well assay plate, the plates were wrapped in Saran wrap with a damp paper towel, and incubated overnight in a refrigerator at 2–8° C. The wells were emptied, washed 3 times using a Wheaton self filling syringe set to deliver 250 µµl/well of wash buffer (containing 500 mM Tris, 2 M sodium chloride, buffered to pH 7) and patted dry. Subsequently, 200 µl of blocking buffer (1% bovine serum albumin solution) was added to each well to block nonspecific sites, 50 µl of the sample was added to each well and the plates were incubated for a minimum of 1 hour at room temperature while mixing on a platform shaker. The wells were again emptied and patted dry, and 50 µl of standard and sample solutions were added. The plates were then covered and incubated for two hours at room temperature. The wells of the plate were again emptied, washed four times with wash buffer and patted dry. Fifty (50) gl of biotinylated antibody (mouse monoclonal 8Cl raised against rhNGF) were added to each well, the plates were covered, and incubated for two hours. The wells of the plates were emptied, washed and dried as described above and 50 µl of horseradish peroxidase-conjugated streptavidin was added to each well. The plates were covered and incubated for 20 minutes at room temperature while mixing on a platform shaker. The plates were washed five times with wash buffer. After 50 µl of orthophenylenediamine (OPD) substrate buffer were added to each well, the plates were covered and incubated in the dark for 1 hour.

A Vmax Kinetic Microplate (Molecular Devices, Mountain View, Calif.) reader was used to determine the absorbance of each well. For each well, the background absorbance at 650 nm was subtracted from the peak absorbance at 450 nm to yield-the net absorbance. The concentration of NGF in the samples was determined by comparison to an NGF standard curve.

Determination of NGF Activity

The bioactivity of NGF was determined by PC-12 bioassay. The PC-12 bioassay is based on increased metabolic activity of PC-12 pheochromocytoma cells (Greene, *Trends Neurosci.* 7:91, 1986) upon exposure to NGF. The metabolic activity of PC-12 cells was measured by cellular uptake of 3-[4,5 dimethylthiazol-2-yl]-2,5-diphenyltetrazoliumbromide($C_{18}H_{16}N_5Br$) (MTT), which is converted by cellular dehydrogenase into insoluble, intracellular blue crystals.

Each well of a 96-well plate contained about 30,000 PC-12 cells in 50 µl of RPMI-1640 medium (Sigma). Serial dilutions of each sample and standards were, prepared to produce solutions of 0.006 to 400 ng of rhNGF per ml in RPMI-1640 with 0.2% bovine serum albumin (BSA). Fifty microliters of each solution were then added to each well to yield concentrations of 0.003 to 200 ng of NGF per ml and each concentration was assayed in triplicate. After maintaining the plates for 2 days in 5% $CO_2$ at 37° C., 10 µg MTT was added to each well and the plates were incubated for an additional 4 hours. One volume of 20% SDS in 50% dimethylformamide (DMF), pH 4.7, was then added and the plates were wrapped in cellophane, sealed inside plastic bags and incubated overnight at 37° C. The plates were read the next day using a Vmax plate reader set at 575 nm. The ratio of the $ED_{50}$ of the sample curve to the $ED_{50}$ of a standard NGF curve provides a measure of the relative potencies of the two preparations.

EXAMPLE 1

NGF Formulation for Lyophilization

The rhNGF used to prepare the formulations was expressed in insect cells using a baculoviral expression vector and purified by ion-exchange and reverse-phase chromatography as described in Barnett, J., et al., *Exp. Neurol.*, 110:11–24, 1990, incorporated herein by reference.

Aqueous NGF formulations comprising 100 µg/ml NGF, 30 mg/ml sucrose, 30 mg/ml mannitol, 5 mg/ml HSA and 0.3 mg/ml citric acid adjusted to pH 6.0 with NaOH were prepared at room temperature. Following dissolution of the citric acid and sugars in about 70% of the total volume, the pH was adjusted, and the HSA and NGF added with gentle stirring along with sufficient water to make volume.

EXAMPLE 2

Lyophilization of NGF Formulations

The lyophilization stability of the aqueous NGF in the formulations of Example 1 was tested. One ml aliquots of NGF formulations prepared according to Example 1 were placed in 5 ml Type I glass vials covered with lyophilization stoppers. The formulation containing vials were loaded into a freeze dryer chamber (FTS Systems Inc.), which was equilibrated at 5° C. prior to the initiation of freezing. The temperature of the chamber was then lowered to −40° C. Following a 2 hour soak at −40° C., the chamber was evacuated and the pressure was controlled at 80 to 100 milliTorr with a nitrogen sweep. A temperature ramp of 4° C. per hour was performed until a terminal drying temperature of 25° C. was achieved. A final moisture content of between 1 and 2% of the product was attained approximately 30 hours into the cycle.

The freeze-dried powder was stored at 5° C. and reconstituted at room temperature after 3 days with 1 ml of a diluent consisting of 8.7 mg/ml sodium chloride and 1.1 mg/ml citric acid, buffered to pH 5.2. Samples were analyzed for NGF concentration by RP-HPLC. No loss of protein was observed following lyophilization and reconstitution.

The foregoing Examples are presented for illustrative purposes only and should not be construed so as to impart any implied limitations on the scope of the claims. The following claims particularly point out and distinctly claim the subject matter which applicants regard as their invention and are entitled to their fall range of legal equivalents. All patents and publications referred to above are specifically incorporated herein by reference.

I claim:

1. A stable aqueous formulation of nerve growth factor, comprising:
   (a) from about 1 to about 1250 μg/ml of a biologically active form of nerve growth factor;
   (b) from about 30 to about 90 mg/ml of a biologically acceptable bulking agent, wherein the bulking agent comprises a mixture of mannitol and sucrose in a 1:1 mass ratio;
   (c) a buffer in an amount sufficient to maintain the pH of the formulation of about 6.0;
   (d) from about 1 to about 12.5 mg/ml of human serum albumin; and
   (e) water, wherein the formulation is suitable for lyophilization.

2. The formulation of claim 1 further comprising from about 5 to about 10 mg/ml of a biologically acceptable salt.

3. The formulation of claim 1 lyophilized to reduce the moisture content to less than about 2% by weight.

4. A method of storing biologically active nerve growth factor, comprising:
   (c) providing the nerve growth factor in an aqueous formulation according to claim 1; and
   (f) lyophilizing the aqueous formulation to a moisture content of less than about 2% by weight.

5. An aqueous formulation of nerve growth factor comprising from about 100 to about 1000 μg/ml biologically active nerve growth factor, from about 30 to about 90 mg/ml a mixture of mannitol and sucrose in a 1:1 mass ratio, from about 1 to about 12.5 mg/ml of human serum albumin, and buffer sufficient to maintain the pH of about 6.0.

6. The formulation of claim 5 comprising from about 15 to about 45 mg/ml sucrose and from about 15 to about 45 mg/ml mannitol.

7. The formulation of claim 5 wherein the buffer is a citrate buffer.

8. A lyophilized composition comprising from about 0.001 to about 1.25 parts by weight biologically active nerve growth factor, from about 30 to about 90 parts by weight sugar comprising a mixture of mannitol and sucrose in a 1:1 mass ratio, from about 0.001 to about 1.25 parts by weight human serum albumin, and less than about 1 part by weight water.

9. A kit for reconstituting an active nerve growth factor formulation comprising, as a first component, a lyophilized composition comprising:
   from about 30 to about 90 parts by weight sugar comprising a mixture of mannitol and sucrose in a 1:1 mass ratio, from about 0.001 to about 1.25 parts by weight human serum albumin, and less than about 1 part by weight water;
   and, as a second component, a quantity of reconstituting vehicle sufficient to produce a formulation containing from about 1 to about 1250 μg/ml of a biologically active form of nerve growth factor when combined with said first component.

10. A kit of claim 9 wherein the reconstituting vehicle comprises a sterile aqueous solution of buffer and salt in an amount sufficient to provide an isotonic solution of biologically active nerve growth factor at a pH from about 4.5 to about 6.0 after mixing the reconstituting vehicle with the lyophilized composition.

* * * * *